(12) United States Patent
Jin et al.

(10) Patent No.: US 9,005,648 B2
(45) Date of Patent: Apr. 14, 2015

(54) INORGANICALLY SURFACE-MODIFIED POLYMERS AND METHODS FOR MAKING AND USING THEM

(75) Inventors: Sungho Jin, San Diego, CA (US); Garrett Smith, San Diego, CA (US); Chulmin Choi, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/176,907

(22) Filed: Jul. 6, 2011

(65) Prior Publication Data

US 2012/0010599 A1 Jan. 12, 2012

Related U.S. Application Data

(60) Provisional application No. 61/361,815, filed on Jul. 6, 2010.

(51) Int. Cl.

| | |
|---|---|
| *A61K 31/7088* | (2006.01) |
| *A61K 35/12* | (2006.01) |
| *A61K 35/23* | (2006.01) |
| *A61K 35/32* | (2006.01) |
| *A61K 35/36* | (2006.01) |
| *B32B 15/08* | (2006.01) |
| *B82Y 5/00* | (2011.01) |
| *C08L 23/02* | (2006.01) |
| *C08L 23/06* | (2006.01) |
| *C08L 71/00* | (2006.01) |
| *A61K 35/28* | (2006.01) |
| *A61K 38/00* | (2006.01) |

(52) U.S. Cl.
CPC ............. *A61K 31/7088* (2013.01); *A61K 35/32* (2013.01); *A61K 35/545* (2013.01); *B32B 15/08* (2013.01); *B82Y 5/00* (2013.01); *C08L 23/02* (2013.01); *C08L 23/06* (2013.01); *C08L 71/00* (2013.01); *A61K 35/28* (2013.01); *B32B 2535/00* (2013.01); *C08G 2650/40* (2013.01); *A61K 38/00* (2013.01)

(58) Field of Classification Search
CPC ..... C08L 2666/02; C08L 23/02; C08L 23/06; C08L 71/00; A61K 35/32; A61K 35/33; A61K 35/35; A61K 35/36; A61K 35/37–35/413; A61K 35/44; A61K 38/18; A61K 8/29; A61K 8/606; A61K 8/65
USPC .............. 514/7.6; 424/130.1, 1.11, 484, 93.3, 424/93.7, 422, 423
See application file for complete search history.

(56) References Cited

FOREIGN PATENT DOCUMENTS

| | | | |
|---|---|---|---|
| WO | WO 2008/066965 | * | 6/2008 |
| WO | WO 2010/003062 | * | 1/2010 |

OTHER PUBLICATIONS

Yao et al., Nanstructured metal coatings on polymers increase osteoblast attachment, 2007, International Journal of Nanomedicine, 2, 483-492.*
Oh et al., Growth of nano-scale hydroxyapetite using chemically treated titanium oxide nanotubes, 2005, Biomaterials, 26, 4938-4943.*
Cortes et al., "The Tensile and Fatigue Properties of Carbon Fiber-reinforced PEEK-Titanium Fiber-metal Laminates", Journal of Reinforced Plastics and Composites, Oct. 2004, vol. 23, No. 15, pp. 1615-1623.
Han et al., "The electron beam deposition of titanium on polyetheretherketone (PEEK) and the resulting enhanced biological properties", Biomaterials, 31, 2010, 3465-3470.
Liu et al., "Contact mechanics of metal-on-metal hip implants employing a metallic cup with a UHMWPE backing", Proc. Instn. Mech. Engrs., J. Engineering in Medicine, 2003, vol. 217, Part H, pp. 207-213.
Pohle et al. "Processing of Three-Dimensional Laser Sintered Polyetheretherketone Composites and Testing of Osteoblast Proliferation in vitro," Macromolecular Symp., 2007, 253, pp. 65-70.
Sagomonyants, "The in vitro response of human osteoblasts to polyetheretherketone (PEEK) substrates compared to commercially pure titanium," Biomaterials, Apr. 29, 2008, 11:1563-72.
Yao et al., "Nanostructured metal coatings on polymers increase osteoblast attachment," International Journal of Nanomedicine, 2007:2(3), pp. 487-492.

* cited by examiner

*Primary Examiner* — Richard Schnizer
*Assistant Examiner* — Alma Pipic
(74) *Attorney, Agent, or Firm* — Gregory P. Einhorn; Greer Burns & Crain Ltd.

(57) ABSTRACT

In alternative embodiments, the invention provides articles of manufacture comprising biocompatible nanostructures comprising PolyEther EtherKetone (PEEK) surface-modified (surface-nanopatterned) to exhibit nanostructured surfaces that promote osseointegration and bone-bonding for, e.g., joint (e.g., knee, hip and shoulder) replacements, bone or tooth reconstruction and/or implants, including their use in making and using artificial tissues and organs, and related, diagnostic, screening, research and development and therapeutic uses, e.g., as primary or ancillary drug delivery devices. In alternative embodiments, the invention provides biocompatible nanostructures that promote osseointegration and bone-bonding for enhanced cell and bone growth and e.g., for in vitro and in vivo testing, restorative and reconstruction procedures, implants and therapeutics.

38 Claims, 18 Drawing Sheets

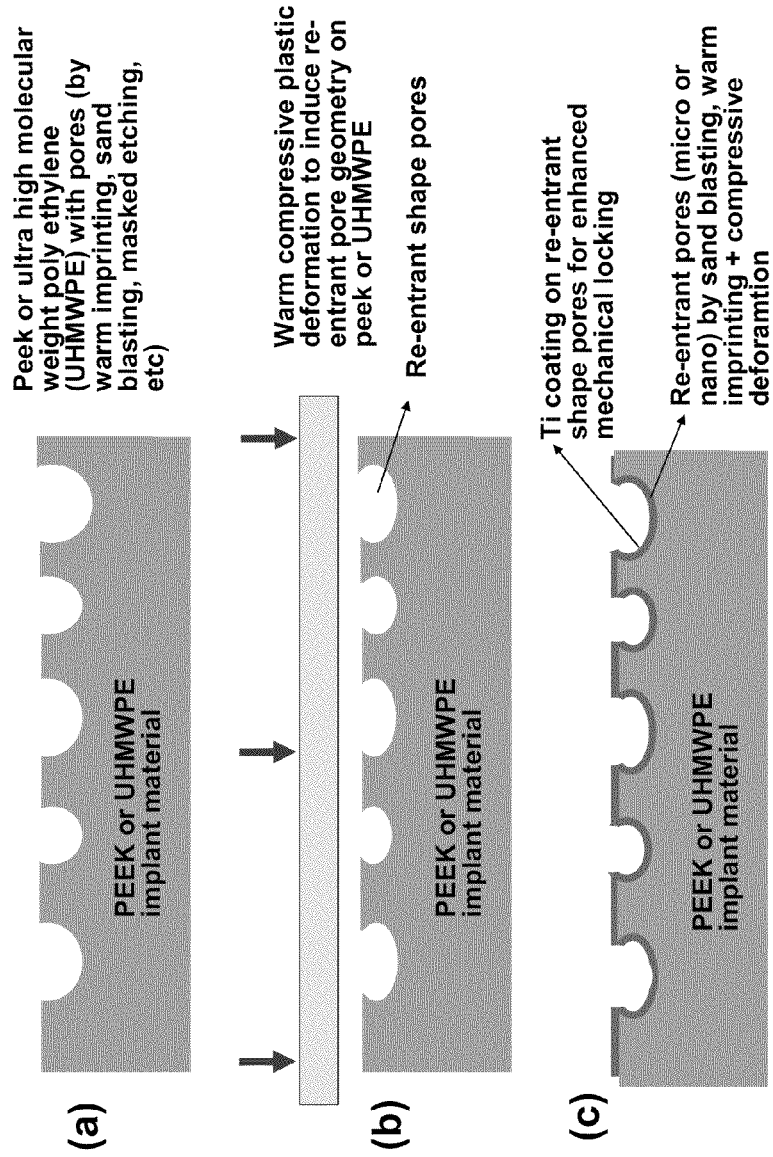

US 9,005,648 B2

INORGANICALLY SURFACE-MODIFIED POLYMERS AND METHODS FOR MAKING AND USING THEM

CROSS REFERENCE TO RELATED APPLICATIONS

This U.S. utility patent application claims benefit of priority under 35 U.S.C. §119(e) to U.S. Provisional Patent Application Ser. No. 61/361,815, filed Jul. 6, 2010. The contents of this application is expressly incorporated herein by reference in its entirely for all purposes.

FIELD OF THE INVENTION

In alternative embodiments, the invention provides articles of manufacture comprising biocompatible nanostructures comprising PolyEther EtherKetone (PEEK) or ultra-high-molecular-weight polyethylene (UHMWPE) surface-modified (surface-nanopatterned) to exhibit nanostructured surfaces that promote osseointegration and bone-bonding for, e.g., joint (e.g., knee, hip and shoulder) replacements, bone or tooth reconstruction and/or implants, including their use in making and using artificial tissues and organs, and related, diagnostic, screening, research and development and therapeutic uses, e.g., as primary or ancillary drug delivery devices. In alternative embodiments, the invention provides biocompatible nanostructures that promote osseointegration and bone-bonding for enhanced cell and bone growth and e.g., for in vitro and in vivo testing, restorative and reconstruction procedures, implants and therapeutics.

BACKGROUND OF THE INVENTION

PolyEther EtherKetone (PEEK) is increasingly being used in spinal implants and investigated as a biomaterial for orthopedic implants because of its mechanical toughness, resistance to thermal and chemical degradation and non-toxicity. Its main advantages over titanium are its x-ray translucence and elastic modulus similar to that of bone. PEEK can be easily viewed with radiography and magnetic resonance to assess implant positioning and stability. It reduces stress shielding in bone and bone resorption, which are common problems from implanted metals with mismatched elasticity properties. PEEK is only now beginning to be explored as a material for joint replacements. It has been shown as an excellent material for articulation in the joint; however, it does not interface well with bone. There is a need for chemically or micro/nanostructurally modified PEEK surfaces which adhere strongly to the PEEK substrate and bond well with bone

SUMMARY

In alternative embodiments the invention provides products of manufacture comprising a thermoplastic polymer or a thermoplastic polymer, or a PolyEther EtherKetone (PEEK), a PolyEtherKetoneKetone (PEKK), a PolyEther EtherKetone (PEEK), an ultra-high-molecular-weight polyethylene (UHMWPE), a thermoplastic polymer as set forth in Table 1, a combination thereof or an equivalent material thereof (e.g., see Table 1, below), and having a biocompatible surface, wherein optionally the product of manufacture substantially comprises or consists essentially of (excepting its biocompatible surface) a thermoplastic polymer, or a PolyEther EtherKetone (PEEK), a PolyEtherKetoneKetone (PEKK), a PolyEther EtherKetone (PEEK), an ultra-high-molecular-weight polyethylene (UHMWPE), a thermoplastic polymer as set forth in Table 1, a combination thereof or an equivalent material thereof, and wherein at least a portion of, or part of, or substantially all, or all of, the surface area of the biocompatible surface comprises or is covered or coated by a structure or structures comprising:

(a) (i) a biocompatible material, which optionally comprises a metal or a metal alloy, and/or a stainless steel or a ceramic, and optionally the metal or a metal alloy comprises Ti, Zr, Hf, Nb, Ta, Mo and/or W metal material, a Ti, Zr, Hf, Nb, Ta, Mo and/or W alloy, a Ti, Zr, Hf, Nb, Ta, Mo and/or W oxide or nitride;

(ii) a plurality of nanotubular structures that are between about 70 to 200 nanometers (nm) in diameter, or between about 60 to 150 nm in diameter, or about 60, 65, 70, 75, 80, 85, 90, 95, 100, 105, 110, 115, 120, 125, 130, 135, 145, 150 155, 165, 170, 175, 180, 185, 190, 200 or more nanometers (nm) in diameter, (iii) a plurality of nanowires, nano-lines or nano-grooves having a spacing of between about 70 to 200 nanometers (nm), or between about 60 to 150 nm, or alternatively between about 5 to 15 nm diameter, or between about 5 to 150 nm in diameter, or about 60, 65, 70, 75, 80, 85, 90, 95, 100, 105, 110, 115, 120, 125, 130, 135, 145, 150 155, 165, 170, 175, 180, 185, 190, 200 or more nanometers (nm) in diameter, or (iv) a combination of the nanotubular structures of (ii) and the nanowires, nano-lines or nano-grooves of (iii);

(b) the product of manufacture of (a), wherein a portion of, or all of, the nanotubular structures comprise nanotubes;

(c) the product of manufacture of (a) or (b), wherein the nanotubular structures, nanowires, nano-lines or nano-grooves comprise a metal or a metal alloy, and/or a stainless steel or a ceramic, and/or the biocompatible surface comprises a metal or a metal alloy, and/or a stainless steel or a ceramic, or a polymer;

(d) the product of manufacture of (c), wherein the metal or a metal alloy comprises Ti, Zr, Hf, Nb, Ta, Mo and/or W metal material, a Ti, Zr, Hf, Nb, Ta, Mo and/or W alloy, a Ti, Zr, Hf, Nb, Ta, Mo and/or W oxide or nitride;

(e) the product of manufacture of any of (a) to (d), wherein the nanotubular structures, nanowires, nano-lines or nano-grooves are straight, curved and/or bent, and optionally the nanotubular structures, nanowires, nano-lines or nano-grooves are fixed or loosely placed, or a combination thereof, on the biocompatible surface;

(f) the product of manufacture of any of (a) to (e), wherein at least a portion of, or all of, the nanotubular structures, nanowires, nano-lines and/or nano-grooves are arranged as an array, and optionally the nanotubular structures, nanowires, nano-lines and/or nano-grooves are arranged as three-dimensional network scaffolds;

(g) the product of manufacture of any of (a) to (f), wherein at least a portion of, or all of, the nanotubular structures, nanowires, nano-lines or nano-grooves comprise a cell, wherein optionally the cell is suitable for implantation and/or regeneration of a bone and/or a joint tissue in a subject, and optionally the cell is an osteoblast, a stem cell or a mesenchymal stem cell (MSC);

(h) the product of manufacture of any of (a) to (g), wherein at least a portion of, or all of, the nanotubular structures, nanowires, nano-lines or nano-grooves comprise one or more biologically active agents, or an osteogenic inducing agent, or a therapeutic drug, a growth factor, a protein, an enzyme, a hormone, a nucleic acid, an RNA, a DNA, a gene, a vector, a phage, an antibiotic, an antibody, a small molecule, a radioisotope, a magnetic nanoparticle and/or a particle;

(i) the product of manufacture of any of (a) to (h), wherein the nanotubular structures, nanowires, nano-lines or nano-grooves are between about 70 to 200 nanometers (nm) in diameter or width, or between about 60 to 150 nm in diameter or width, or have a spacing between the nanowires, nano-lines or nano-grooves of between about 70 to 200 nanometers (nm), or between about 60 to 150 nm, or about 60, 65, 70, 75, 80, 85, 90, 95, 100, 105, 110, 115, 120, 125, 130, 135, 145, 150 155, 165, 170, 175, 180, 185, 190, 200 or more nanometers (nm) in diameter or width; and optionally comprise a mesenchymal stem cell (MSC) or a human mesenchymal stem cell (hMSC); or embryonic stem cell, or (j) the product of manufacture of any of (a) to (h), wherein the nanotubular structures, nanowires, nano-lines or nano-grooves are about 100 nanometers (nm) in diameter or width, or are between about 80 to 120 nm in diameter or width, or have a spacing between the nanowires, nano-lines or nano-grooves of about 100 nanometers (nm), or have a spacing between them of about 80 to 120 nm, or having a spacing between them of about 60, 65, 70, 75, 80, 85, 90, 95, 100, 105, 110, 115, 120, 125, 130, 135, 145, 150 155, 165, 170, 175, 180, 185, 190, 200 or more nanometers (nm); and optionally comprise a "regular" or fully differentiated or partially differentiated osteoblast cell, or wherein the nanotubular structures or nanotubes have a diameter of between about 5 to 15 nm range and have between about 0.1 to 3 micrometer height.

In alternative embodiments of the products of manufacture of the invention, at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or all, of the biocompatible surface is covered by a plurality of nanotubular structures, nanowires, nano-lines or nano-grooves.

In alternative embodiments of the products of manufacture of the invention, the biocompatible surface and/or the nanotubular structures, nanowires, nano-lines or nano-grooves comprise: a matrix material; or a Ti, Zr, Hf, Nb, Ta, Mo and/or W metal; or an oxide of a Ti, Zr, Hf, Nb, Ta, Mo and/or W metal; (iii) an alloy of a Ti, Zr, Hf, Nb, Ta, Mo and/or W metal; or a Si, a Si oxide, an Al, an Al oxide, a carbon, a diamond, a noble metal, an Au, an Ag, a Pt and/or an Al, Au, an Ag, a Pt alloy, a polymer or a plastic material, a composite metal, a ceramic, a polymer and/or a combination thereof.

In alternative embodiments products of manufacture of the invention further comprise a bone cell, a liver cell, a kidney cell, a blood vessel cell, a skin cells, a periodontal cell or a periodontal tissue cell, a stem cell, an organ cell, or wherein the cell is a bone cell, a liver cell, a kidney cell, a blood vessel cell, a skin cells, an organ cell; or, further comprise a plurality of cells, wherein the cells comprise bone cells, liver cells, liver parenchymal cells, endothelial cells, adipocytes, fibroblastic cells, Kupffer cells, kidney cells, blood vessel cells, skin cells, periodontal cells, odontoblasts, dentinoblasts, cementoblasts, enameloblasts, odontogenic ectomesenchymal tissue, osteoblasts, osteoclasts, fibroblasts, and other cells and tissues involved in odontogenesis or bone formation and/or stem cells, and other human or animal organ cells, or the cells are embryonic or adult stem cells, or a combination thereof. The cell can be a human or an animal cell, or the product of manufacture, further comprises a human or an animal cell.

In alternative embodiments products of manufacture of the invention further comprise a hydroxyapatite, a bio-degradable polymer, or a bio-compatible or bio-inert bone cement; or further comprise a biological agent or a therapeutic composition, or an osteogenic inducing agent, or a growth factor, a collagen, a nucleic acid, an antibiotic, a hormone, a drug, a magnetic particle, a metallic particle, a ceramic particle, a polymer particle and/or a drug delivery particle.

In alternative embodiments products of manufacture of the invention further comprise nanotubular structures or nanotubes made, e.g., by anodization or by patterned chemical etching or a combination thereof.

In alternative embodiments products of manufacture of the invention further comprise a nanodepot comprising a metallic or oxide material, hydroxyapatite, a bio-degradable polymer, or a bio-compatible or bio-inert bone cement; or further comprise, or comprise an osteogenic inducing agent, or a biological agent or a therapeutic composition, or a growth factor, a collagen, a nucleic acid, an antibiotic, a hormone, a drug, a magnetic particle, a metallic particle, a ceramic particle, a polymer particle and/or a drug delivery particle.

In alternative embodiments products of manufacture of the invention further comprise a matrix material comprising a nanodepot, or a nanodepot, made of (comprising a) metal, oxide, hydroxyapatite, bio-degradable polymer, bio-compatible or bio-inert bone cement, wherein one or more of components selected from a list of the stem cells, osteogenic inducing agent, or the biological agent or therapeutic composition, or growth factor, collagen, nucleic acid, antibiotic, hormone, drug, magnetic particle, metallic particle, ceramic particle, polymer particle or drug delivery particle are stored in a nanotubular structure or a nanotube cavity, or are stored in spacing between adjacent nanotubular structures, nanowires, nano-lines or nano-grooves.

The invention provides compositions and/or delivery devices comprising a product of manufacture of the invention, wherein optionally the composition and/or delivery device comprises a hydroxyapatite, a bio-degradable polymer, or a bio-compatible or bio-inert bone cement; or further comprises, or comprises stem cells, an osteogenic inducing agent, or a biological agent or a therapeutic composition, or a growth factor, a collagen, a nucleic acid, an antibiotic, a hormone, a drug, a magnetic particle, a metallic particle, a ceramic particle, a polymer particle and/or a drug delivery particle.

The invention provides medical implants or replacements, orthopedic (orthopedic) or joint implants or replacements or dental implants or replacements comprising a product of manufacture of the invention, and optionally the orthopedic (orthopedic) or joint implant or replacement or dental implant or replacement comprises a plurality of cells, and optionally the joint implant is a knee, hip or shoulder implant or replacement, and optionally the cells comprise bone cells, liver cells, liver parenchymal cells, endothelial cells, adipocytes, fibroblastic cells, Kupffer cells, kidney cells, blood vessel cells, skin cells, periodontal cells, odontoblasts, dentinoblasts, cementoblasts, enameloblasts, odontogenic ectomesenchymal tissue, osteoblasts, osteoclasts, fibroblasts, and other cells and tissues involved in odontogenesis or bone formation and/or stem cells, and other human or animal organ cells, or the cells are embryonic or adult stem cells, or a combination thereof.

The invention provides methods for inducing, enhancing and/or prolonging the bone-forming capacity of a "regular", or a fully differentiated or a partially differentiated osteoblast cell or cell of osteogenic lineage, comprising implanting, growing and/or culturing an osteoblast cell or a cell of osteogenic lineage in a product of manufacture of the invention.

The invention provides methods for selectively releasing a therapeutic, an imaging, a drug or a biological agent in a subject, the method comprising (a) implanting a product of manufacture of the invention, in a subject, wherein the product of manufacture comprises a therapeutic, an imaging, a drug or a biological agent in a liquid or colloidal composition; and, (b) contacting the product of manufacture with ultrasonic or magnetic agitation of the liquid or colloidal composition, wherein the biological agent is released from the product of manufacture;

and optionally the magnetic nanoparticle is selected from the group consisting of iron-oxide particles of magnetite ($Fe_3O_4$) or maghemite ($\gamma$-Fe2O3), and optionally the magnetic nanoparticle is about 5 to 50 nm in average diameter.

The invention provides products of manufacture of the invention, fabricated for in vivo hard tissue applications, which optionally can be for orthopedics, joint replacements, hip stems, knee implants, shoulder replacements, dental implants, craniofacial implants; and for spine applications, cervical, thoracic, and/or lumbar spinal instrumentation, interbody vertebral cages, pedicle screws and the like.

The invention provides products of manufacture of the invention, fabricated for in vivo applications including trauma, fixation devices, which optionally can be for internal, external or rods. The invention provides products of manufacture of the invention, fabricated for in vivo applications, which optionally can be fabricated as a bone substitute material, bone void filler, and/or bone graft material.

The invention provides products of manufacture of the invention, fabricated for in vivo soft tissue applications, which optionally can be for catheters that need to be anchored in skin, implantable devices that promote cell growth, and/or biosensors that reduce fibrotic capsule which blocks electrical/chemical signal.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

BRIEF DESCRIPTION OF THE DRAWINGS

The drawings are illustrative of embodiments of the invention and are not meant to limit the scope of the invention as encompassed by the claims. The advantages, nature and additional features of the invention will appear more fully upon consideration of the illustrative embodiments described in the accompanying drawings.

FIG. 2A illustrates an exemplary mould (stamp) for nano-imprinting after thermoplastic heating (or coat with UV-sensitive resist and imprint pattern (protruding or recessed), and a nano-imprinted PEEK or other biocompatible polymers like UHMWPE; FIG. 2B illustrates deposited Ti, $TiO_2$, $ZrO_2$, $HfO_2$, Ta, Ta-oxide or other cell-growth enhancing coating (by sputtering, plasma spray, CVD deposition) on PEEK surface. The Ti surface may optionally anodized or nano-patterned into $TiO_2$ nanotubes for enhanced cell adhesion/growth or stem cell control; FIG. 2C illustrates osteoblast, stem cells or other cells (or bone, cartilage tissue) adhered and growing on Ti coated (or Co—Cr or other biocompatible metal or ceramic), imprint patterned PEEK or UHMWPE surface.

FIG. 3A illustrates a nano-imprinted PEEK or other biocompatible polymer with a deposited Ti or other cell-growth enhancing coating (e.g., by sputtering, plasma spray, CVD deposition) on a patterned or flat PEEK surface; FIG. 3B illustrates anodized TiO2 nanotubes on a Ti-deposited surface on a PEEK substrate; FIG. 3C illustrates osteoblasts, stem cells or other cells (or bone or cartilage tissue) adhered and growing on TiO2 nanotubes.

FIG. 4(a) illustrates an exemplary three-dimensional mould for nano-imprinting of complex geometry onto PEEK or other biocompatible polymer materials like or UHMWPE to exhibit nanosurface structure; FIG. 4(b) illustrates an exemplary nano-imprinted+Ti coated or Ta coated by sputtering or evaporation (or additionally anodized or hydrothermal treated for $TiO_2$ nanotube surface) for enhanced cell adhesion and growth, or stem cell control); FIG. 4(c) illustrates an example SEM micrograph showing approximately 80 to 100 nm diameter $TiO_2$ nanotubes grown by anodization of deposited Ti coating; FIG. 4(d) illustrates exemplary 8 nm diameter TiO2 nanotubes grown on deposited Ti film by hydrothermal process at about 100° C. to about 150° C. (TEM image (left) and SEM image (right))

FIG. 17 illustrates exemplary "re-entrant" Ti or $TiO_2$ coating: FIG. 17(a) illustrates PEEK, PEKK, UHMWPE, etc. implant with surface pores (in alternative embodiment made by warm imprinting, sand blasting, masked etching, and the like); FIG. 17(b) illustrates the (optional) embodiment comprising plastic deformation to partially squash the polymer implant surface and induce re-entrant pore geometry on PEEK, PEKK, UHMWPE, etc.; FIG. 17(c) illustrates Ti, Ta, Zr, Hf, or their oxides, and the like, coating on re-entrant shape pore surface for enhanced mechanical locking.

Figure 1:
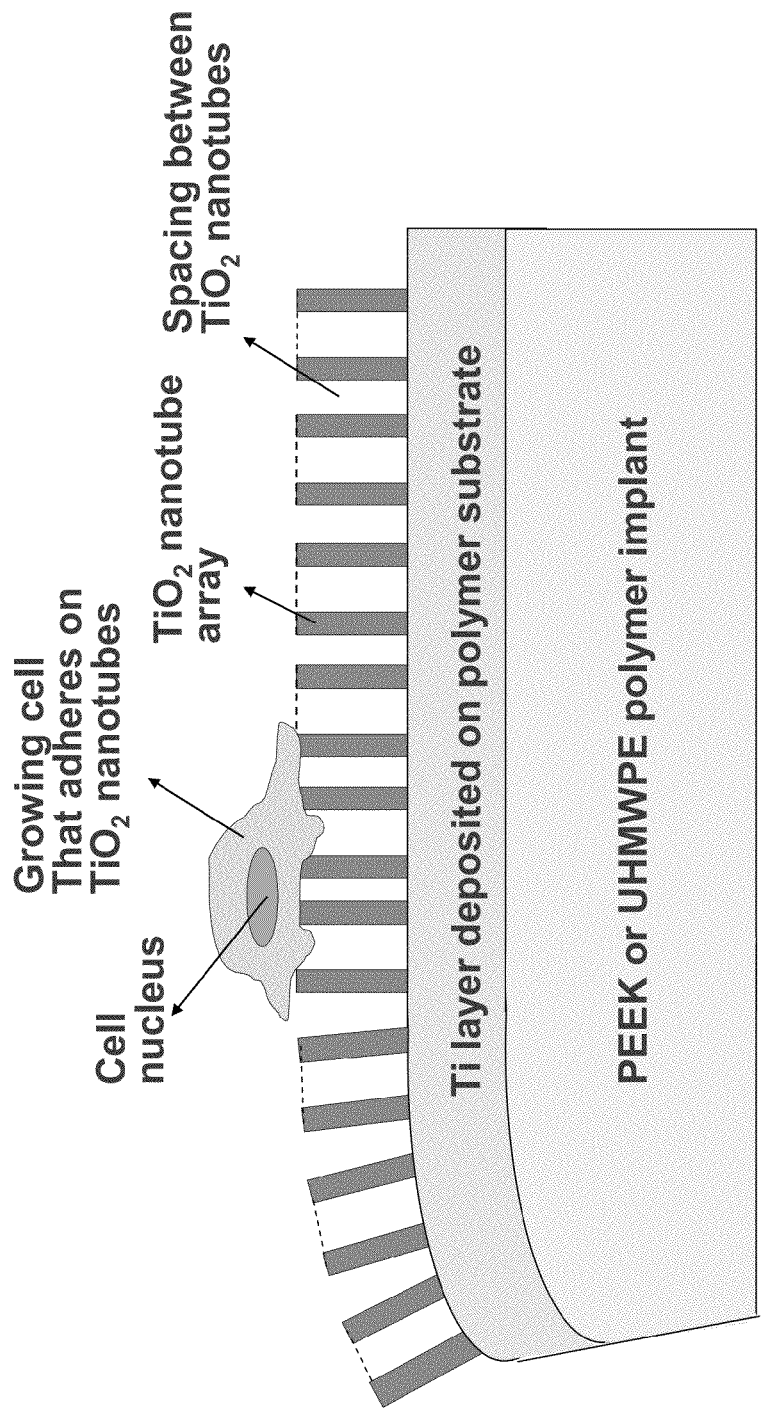
FIG. 1 illustrates enhanced osteoblast cell adhesion and growth on conformationally placed $TiO_2$ nanotubes by anodization of deposited Ti layer on unpatterned or patterned thermoplastic polymer, PolyEther EtherKetone (PEEK), PolyEtherKetoneKetone (PEKK), an ultra-high-molecular-weight polyethylene (UHMWPE), thermoplastic polymer as set forth in Table 1, any combination thereof or equivalent material thereof (although only PEEK and UHMWPE are illustrated) (flat or three-dimensionally shaped) or various other polymer or glass surface.
Figure 2:
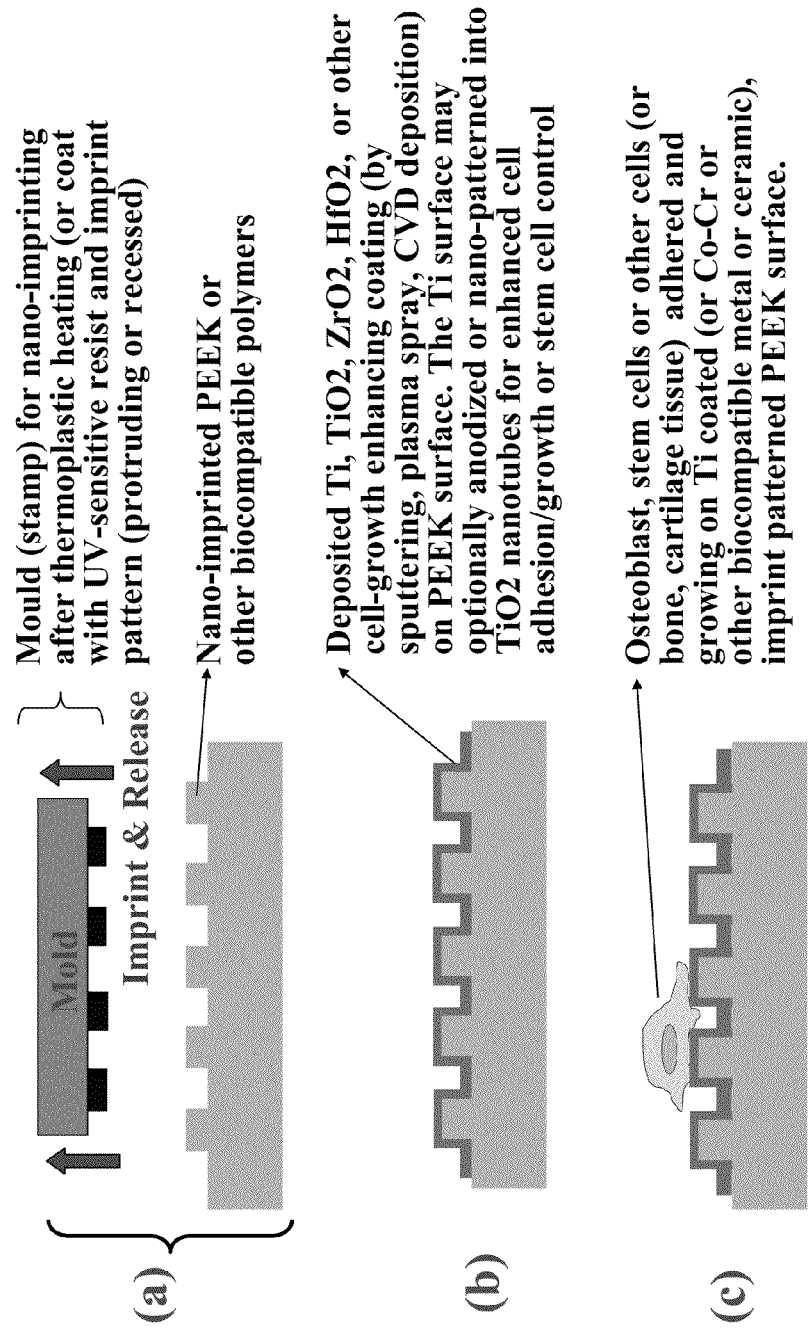
FIG. 2 illustrates Nano-patterned PEEK, PEKK, UHMWPE, thermoplastic polymer as set forth in Table 1, any combination thereof or equivalent material thereof (although only PEEK is illustrated)+cell-growth enhancing coating of Ti or $TiO_2$ coating or other layer coating.
Figure 3:
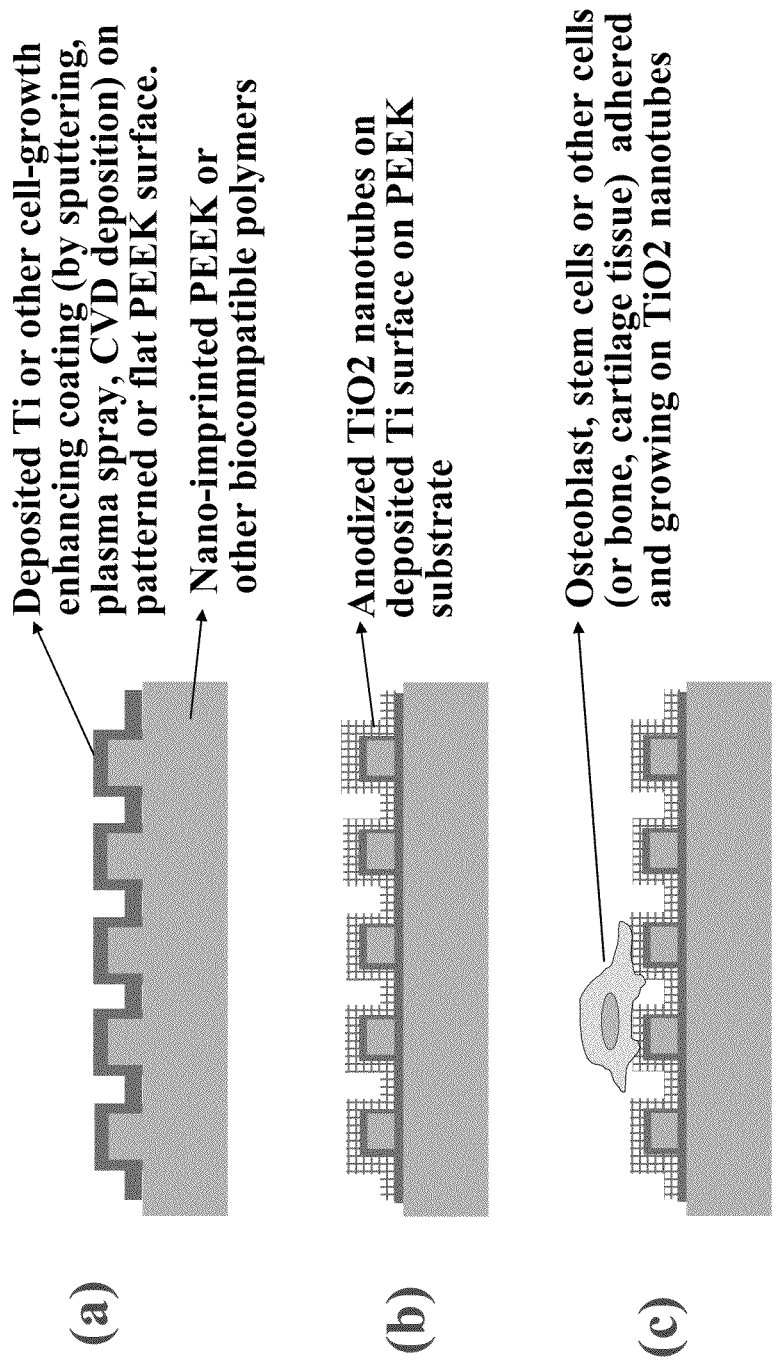
FIG. 3 illustrates surface-modified PEEK, PEKK, UHMWPE, thermoplastic polymer as set forth in Table 1, any combination thereof or equivalent material thereof (although only PEEK is illustrated) with nano-imprinted pattern coated with Ti, Zr, etc., and anodized to form conformal nanotubes.

The drawings are further described below.

It is to be understood that the drawings are for purposes of illustrating the concepts of the invention and are not to scale.

DETAILED DESCRIPTION

In alternative embodiments, the invention provides surface-nanopatterned polymers for e.g., joint (e.g., knee, hip and shoulder) replacement, bone or tooth reconstructive and/or implant applications, and the like, comprising a PolyEther EtherKetone (PEEK), a PolyEtherKetoneKetone (PEKK), a PolyEther EtherKetone (PEEK) or an ultra-high-molecular-weight polyethylene (UHMWPE), or equivalent, or a combination thereof, material surface-modified (surface-nanopatterned) to exhibit nanostructured surfaces that promote osseointegration and bond-bonding.

In alternative embodiments, PEEK, PEKK or UHMWPE surface modification is done by coating the polymer with layers of Ti or Ti oxide, or similar biocompatible metals, alloys and oxides which are nanostructured by various means (e.g., nano-imprinting, patterned-mask-deposition followed by preferential etching or sand blasting etc). Whereas polymers integrate poorly with bone, the invention's nanostructured coating enhances cell adhesion and promotes preferential stem cell differentiation to bone cells. The invention thus enables use of elastically bone-like and x-ray translucent PEEK for knee prostheses and other joint replacements or bone-anchored implants, e.g., hip and shoulder replacements, dental implants.

In alternative embodiments, products of manufacture of the invention improve the osseointegration of PEEK implants by chemical and structural modifications of its surface. In alternative embodiments, the invention provides a chemically and/or microstructurally modified PEEK surface with a strongly adherent coating to the PEEK surface substrate that has favorable interfacial bonding properties with bone.

In alternative embodiments, products of manufacture of the invention comprise a thermoplastic polymer such as PEEK, e.g., DYNEEMA™ (DSM Dyneema LLC, Stanley, N.C.) or SPECTRA™ (Honeywell, Colonial Heights, Va.), or any of the thermoplastic polymers listed below, and are made to comprise a nanostructured surface modification which promotes osseointegration.

TABLE 1

Exemplary thermoplastics used to make products of manufacture of the invention

Acrylonitrile butadiene styrene (ABS)
Acrylic (PMMA)
Celluloid
Cellulose acetate
Cycloolefin Copolymer (COC)
Ethylene-Vinyl Acetate (EVA)
Ethylene vinyl alcohol (EVOH)
Fluoroplastics (PTFE, alongside with FEP, PFA, CTFE, ECTFE, ETFE)
Ionomers
Kydex ™, a trademarked acrylic/PVC alloy
Liquid Crystal Polymer (LCP)
Polyacetal (POM or Acetal)
Polyacrylates (Acrylic)
Polyacrylonitrile (PAN or Acrylonitrile)
Polyamide (PA or Nylon)
Polyamide-imide (PAI)
Polyaryletherketone (PAEK or Ketone)
Polybutadiene (PBD)
Polybutylene (PB)
Polybutylene terephthalate (PBT)
Polycaprolactone (PCL)
Polychlorotrifluoroethylene (PCTFE)
Polyethylene terephthalate (PET)
Polycyclohexylene dimethylene terephthalate (PCT)
Polycarbonate (PC)
Polyhydroxyalkanoates (PHAs)
Polyketone (PK)
Polyester
Polyethylene (PE)
Polyetheretherketone (PEEK)
Polyetherketoneketone (PEKK)
Polyetherimide (PEI)
Polyethersulfone (PES)
Polysulfone
Polyethylenechlorinates (PEC)
Polyimide (PI)
Polylactic acid (PLA)
Polymethylpentene (PMP)
Polyphenylene oxide (PPO)
Polyphenylene sulfide (PPS)
Polyphthalamide (PPA)
Polypropylene (PP)
Polystyrene (PS)
Polysulfone (PSU)
Polytrimethylene terephthalate (PTT)
Polyurethane (PU)
Polyvinyl acetate (PVA)

TABLE 1-continued

Exemplary thermoplastics used to make products of manufacture of the invention

Polyvinyl chloride (PVC)
Polyvinylidene chloride (PVDC)
Styrene-acrylonitrile (SAN)

In alternative embodiments, products of manufacture of the invention comprise a thermoplastic polymer such as an ultra-high-molecular-weight polyethylene (UHMWPE). This polymer can be surface modified in a similar way as a PEEK; it is a strong but a thermoplastic polymer that can be softened at about 140° C. for nano-imprinting. UHMWPE (which can be shortened to UHMW), is also known as high-modulus polyethylene (HMPE) or high-performance polyethylene (HPPE), thus reference to UHMWPE also includes any UHMW, HMPE, HPPE or equivalent. In alternative embodiments, thermoplastic polymers with long chains having molecular weights numbering in the millions, e.g., between 2 and 6 million daltons, are used. In alternative embodiments, HDPE molecules can have between 700 and 1,800 monomer units per molecule, whereas UHMWPE molecules can have 100,000 to 250,000 monomers each.

In alternative embodiments, products of manufacture of the invention are made by nano-imprinting or patterned-mask-deposition followed by preferential etching of exposed surface (e.g., using reactive ion etch or chemical etch), or mechanical sand blasting or shot pinning can be utilized.

In alternative embodiments of products of manufacture of the invention the thermoplastic polymer (e.g., a PEEK or UHMWPE) bonds and integrates with bone. For example, in one embodiment an entire knee prosthetic comprises a PEEK or a UHMWPE, with the backside of the nanostructured implant surface-modified to promote bone bonding, and the front side of the implant designed as an articulating joint surface.

In alternative embodiments, protruding or recessed nanostructures (FIG. 1, FIG. 2, FIG. 3 and FIG. 4) of nanopillars, nanopores or nanotubes enhance cell adhesion, and also promotes preferential stem cell differentiation to bone cells. For example, in one embodiment, mesenchymal stem cells are used such that they differentiate to osteoblast cells in a Ti nanotube environment.

Figure 4:
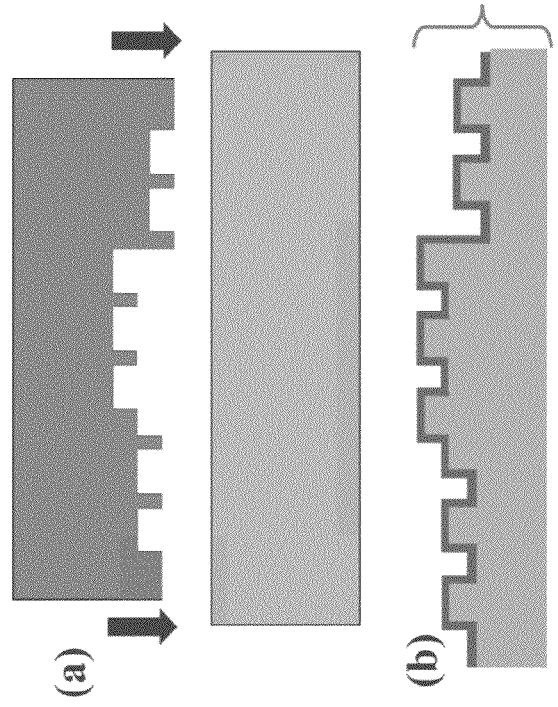
FIG. 4 illustrates an exemplary three dimensional complex nano-imprinting and surface coating with Ti or $TiO_2$ nanotubes.
Figure 4:
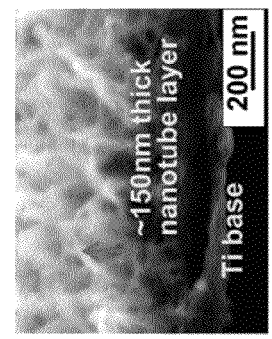
Figure 4:
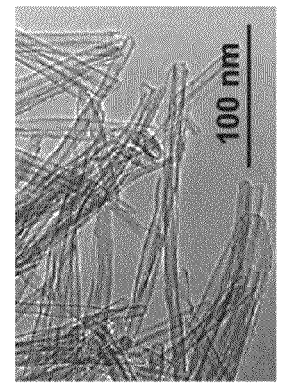
Figure 4:
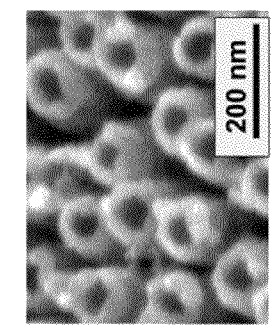
Figure 4E:
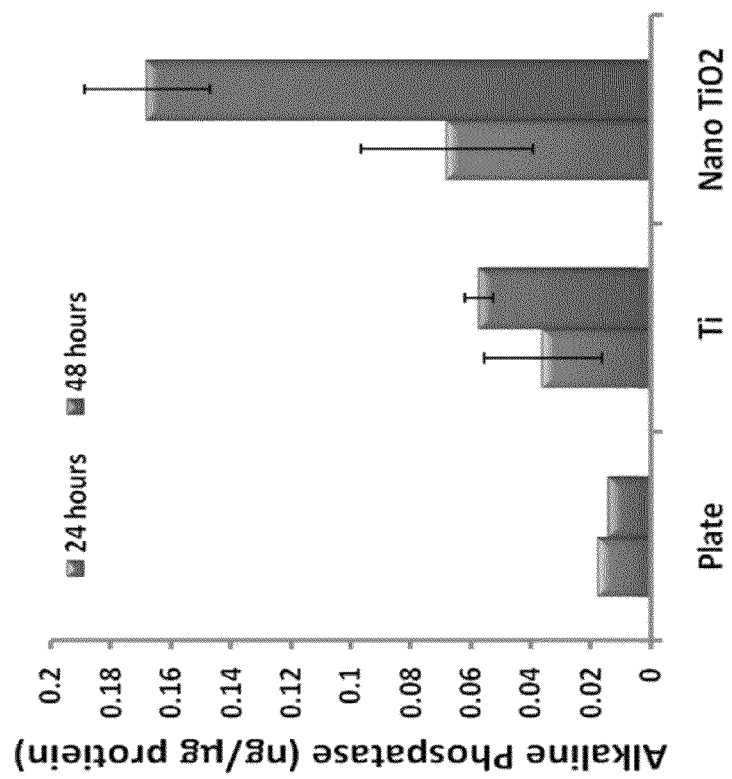
FIG. 4(e) graphically illustrates alkaline phosphatase activity of osteoblast cells cultured on smooth Ti, vs 8 nm diameter $TiO_2$ nanotubes after 24 and 48 h of incubation. The bar graphs show the average±standard error bars.

As illustrated in FIG. 4, eight (8) nm diameter $TiO_2$ nanotubes prepared by hydrothermal process have excellent bone cell growth characteristics, as good as anodized approximately 100 nm diameter vertically aligned TiO2 nanotubes; see the 8 nm TiO2 nanotube data as FIG. 4(d) and FIG. 4(e), comparing with anodized ~100 nm TiO2 nanotubes in FIG. 4(c). As illustrated in FIG. 4(e), the 8 nm diameter nanotube structure provided significantly up-regulated bone forming ability from the MC3T3-E1 mouse osteoblast bone cells with approximately 2 to 3 fold increased alkaline phosphatase (ALP) activity levels, and induced the formation of abundant amounts of bone matrix deposition predominantly consisting of calcium and phosphorous. FIG. 4 illustrates three dimensional complex nano-imprinting and surface coating with Ti or $TiO_2$ nanotubes: (a) Three-dimensional mould for nano-imprinting of complex geometry onto PEEK or other biocompatible polymer materials like or UHMWPE to exhibit nano surface structure; (b) Nano-imprinted+Ti coated or Ta coated by sputtering or evaporation (or additionally anodized or hydrothermal treated for $TiO_2$ nanotube surface) for enhanced cell adhesion and growth, or stem cell control); (c) Example SEM micrograph showing about 80-100 nm diameter $TiO_2$ nanotubes grown by anodization of deposited Ti coating; (d) Example 8 nm diameter $TiO_2$ nanotubes grown on deposited Ti film by hydrothermal process at about 100° C. to about 150° C. (TEM image (left) and SEM image (right)); (e) Alkaline phosphatase activity of osteoblast cells cultured on smooth Ti, vs 8 nm diameter $TiO_2$ nanotubes after 24 and 48 h of incubation. The bar graphs show the average±standard error bars. The 8 nm diameter nanotube structure provided significantly up-regulated bone forming ability from the MC3T3-E1 mouse osteoblast bone cells with about 2 to 3 fold increased alkaline phosphatase (ALP) activity levels, and induced the formation of abundant amounts of bone matrix deposition predominantly consisting of calcium and phosphorous.

Alternatively, these anodized or hydrothermally grown nanotubes can be optionally micro or macro patterned so that 50% or less of the surface area of PEEK or UHMWPE is covered by $TiO_2$ nanotubes for enhanced x-ray radiolucent properties.

In alternative embodiments, surface nanostructured thermoplastic polymers (e.g., a PEEK or UHMWPE) of the invention have a coating, or an additional coating, with a Ti and Ti oxide, Zr, Hf, Nb, Ta, Mo, W, Cr, Cr—Co alloy, stainless steel and their oxides, as well as their alloys, with a thin layer having a thickness of at least 5 nm, and optionally less than 500 nm, so that much of some x-ray penetration with soft x-ray is possible for diagnostic/tracking purposes. These surface coating layers of Ti and Ti oxide, Zr, Hf, Nb, Ta, Mo, W, Cr, Cr—Co alloy, stainless steel and their oxides, as well as their alloys, are bioactive and enhance osseointegration and stem cell differentiation to bone cells.

Figure 5:
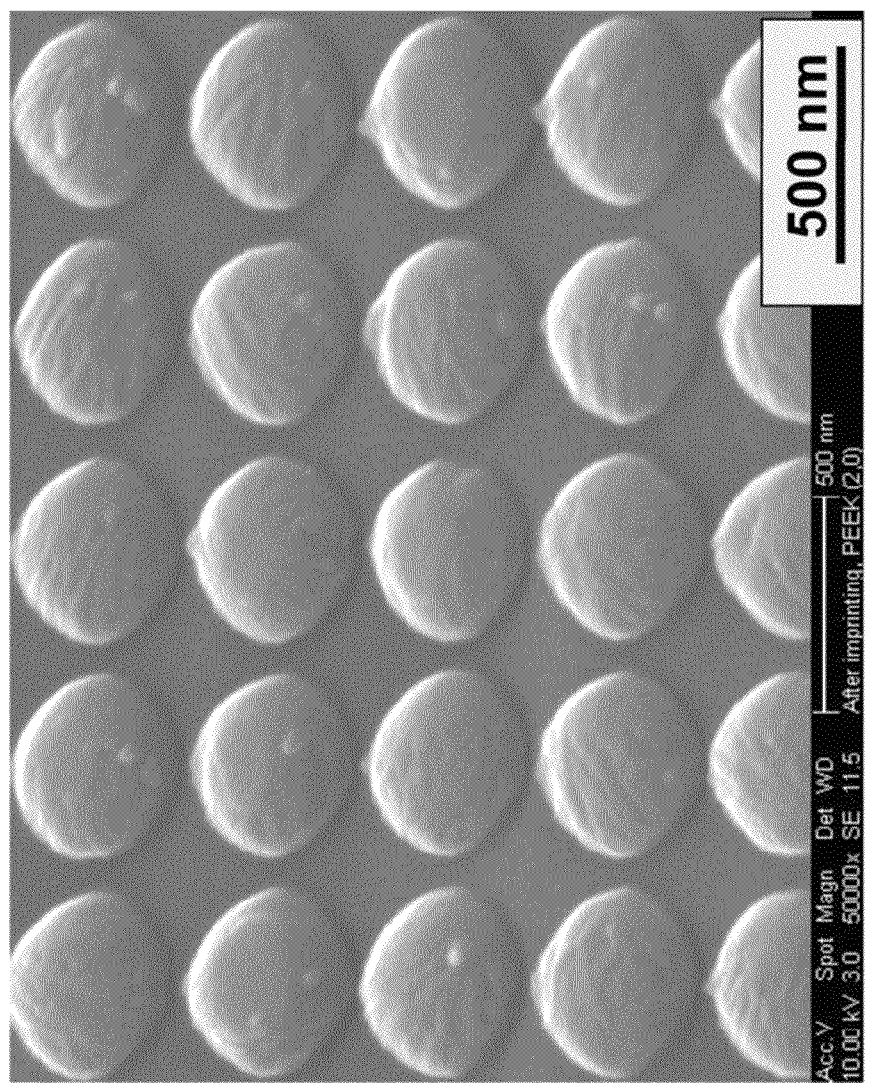
FIG. 5 illustrates island nanopatterned PEEK, PEKK, UHMWPE, thermoplastic polymer as set forth in Table 1, any combination thereof or equivalent material thereof (although only PEEK is illustrated) by imprinting and metal coated.
Figure 6:
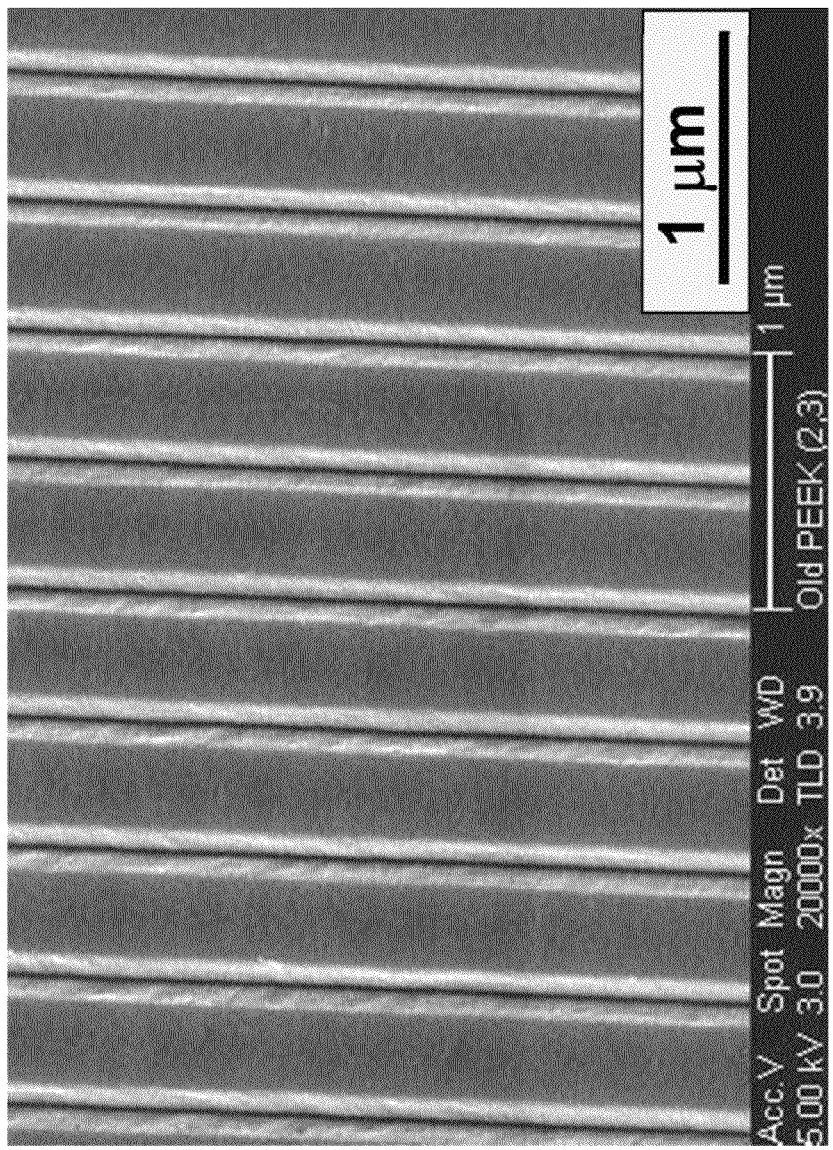
FIG. 6 illustrates line-array nanopatterned PEEK, PEKK, UHMWPE, thermoplastic polymer as set forth in Table 1, any combination thereof or equivalent material thereof (although only PEEK is illustrated) by imprinting and metal coated.
Figure 7:
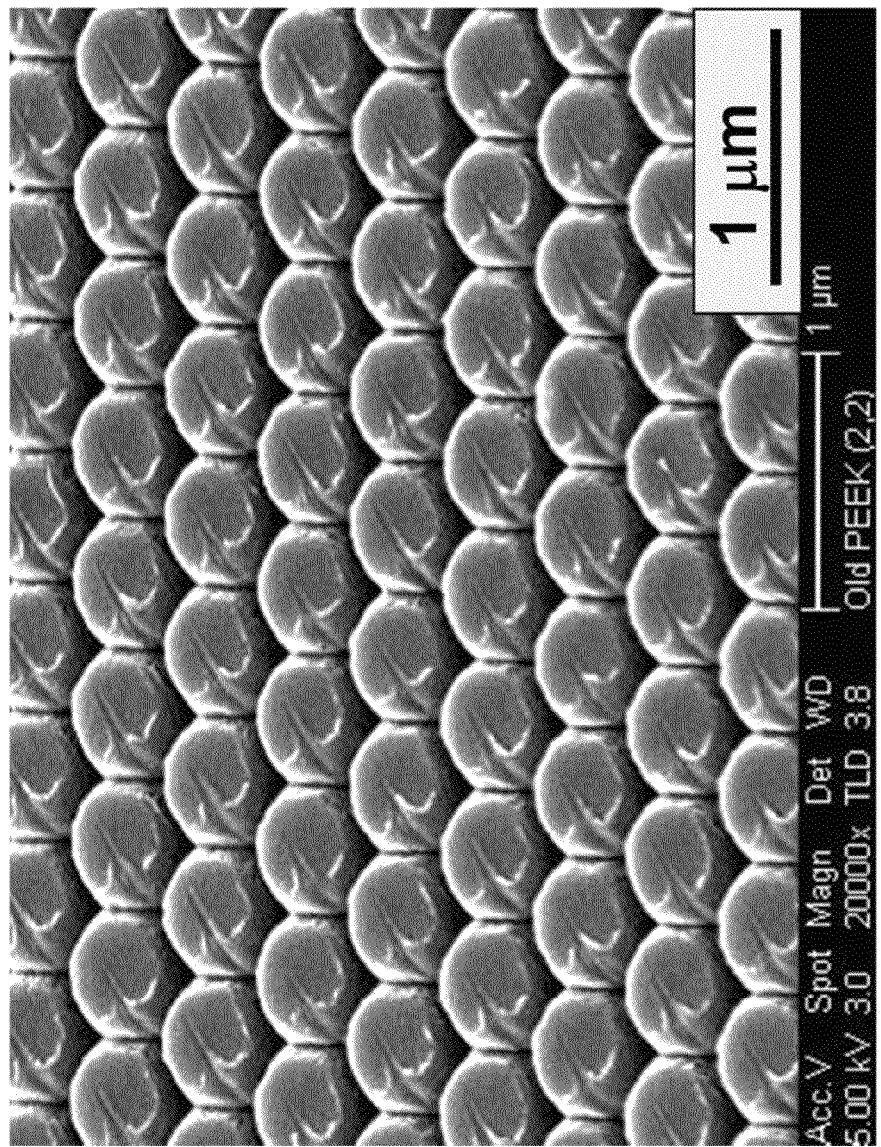
FIG. 7 illustrates island nanopatterned PEEK, PEKK, UHMWPE, thermoplastic polymer as set forth in Table 1, any combination thereof or equivalent material thereof (although only PEEK is illustrated) by imprinting and Ti metal coated for TiO2 nanotube anodization.

An alternative embodiment configuration of the invention is to introduce partially Ti covered surface (or other adherent coating materials), for example, about 20% to 70% of the relevant implant surface is coated with osseointegrating metal film coating, with the remaining 80% to 30% are a bare-surface thermoplastic polymer (e.g., a PEEK or UHMWPE) to provide soft x-ray imaging of the regions with the implants to monitor the soundness of positioning, attachment and osseointegration progress. Examples of nanopatterned PEEK or UHMWPE or equivalents with added Ti coating are shown in SEM micrographs of FIG. 5, FIG. 6 and FIG. 7.

In alternative embodiments of products of manufacture of the invention the thermoplastic polymer (e.g., a PEEK) comprises a surface of, or further comprise an additional nano-structure on a deposited metal layer, including e.g., Ti (or Zr, Hf, Nb, Ta, Mo, W, Cr, and their alloys, Cr—Co alloy, stainless steel), e.g., by using anodization for $TiO_2$ nanotubes or alloy nanotubes having a dimension of about 20-1000 nm diameter and relatively thin (e.g., about 30-500 nm height) nanotube layer for enhanced soft x-ray imaging. In alternative embodiments the presence of anodized $TiO_2$ nanotubes significantly enhances the osseointegration kinetics and the bone-bonding mechanical strength.

In alternative embodiments, nanopillar or nanopore structure, instead of or in addition to, nanotube structures, are fabricated using e.g., a mask-patterned surface modification.

In alternative embodiments, products of manufacture of the invention comprise a metal- or ceramic-coated surface (e.g., a PEEK or a UHMWPE surface). embodiments of products of manufacture the anodized surface can partially cover the relevant implant surface, for example, about 20-70% of the surface can be coated with an osseointegrating nanotube layer, with the remaining about 80-30% bare surface of the thermoplastic polymer (e.g., a PEEK or a UHMWPE) provides soft x-ray imaging of the regions with the implants for monitoring or diagnosis purpose.

In alternative embodiments, products of manufacture of the invention comprise a nanotube pore structure (or the spacing and gap between the nanopillar structures) to store and controllably release biological agents such as stem cells, growth factors (such as bone morphogenic protein), DNA or RNA, antibiotics, or various drugs, and allow them to be slowly released, or remote activated for on-demand release.

In alternative embodiments, products of manufacture of the invention comprise thermoplastic polymer (e.g., a PEEK or a UHMWPE) osseointegration-promoting surface on a joint replacement prosthesis or implant, e.g., a knee, hip and shoulder replacement or implant prostheses, or for any joint replacement or bone-anchored implant, e.g., hip and shoulder replacements, dental implants.

In alternative embodiments, products of manufacture of the invention are made utilizing a novel nano-patterned imprinting stamp which, when placed vertically and impressed with compressive force onto the surface of thermoplastic biomaterials. One example comprises a PEEK near its glass transition temperature (~143° C.), which produces a nano-patterned pillar array or pore array. In alternative embodiments, dimensions of the resultant nano-pillars are in the range of between about 10 to about 5000 nm, or between about 70 to about 1000 nm, or between about 100 to about 700 nm.

In alternative embodiments, after nano-imprinting of the polymer biomaterial, the nano-patterned PEEK, or UHMWPE or equivalents is/are subjected to Scanning Electron Microscopy (SEM) to verify the nanostructures. Then, optionally, a layer of titanium (or Ti oxide, either amorphous, anatase or rutile phase) is sputter coated uniformly onto the nano-patterned surface.

In alternative embodiments, the layer of titanium is varied between 5 nm and 500 nm. The titanium layer can serve a two-fold purpose. First, it coats the hydrophobic thermoplastic polymer (e.g., a PEEK or UHMWPE or equivalents) with a layer of titanium which is both hydrophilic and biocompatible. Second, depending on the thickness of the titanium coating, it allows for additional surface modifications that promote enhanced osseointegration on the titanium coated nanostructured pattern. For example in alternative embodiments an additional surface modification is anodization in hydrofluoric acid for 30 minutes at 20 volts to fabricate titanium dioxide nanotubes on the surface for an enhanced osseointegration effect.

In alternative embodiments, products of manufacture of the invention comprise or are fabricated for in vivo hard tissue applications, including e.g., orthopedics, joint replacements, hip stems, knee implants, shoulder replacements, dental implants, craniofacial implants; and for spine applications, cervical, thoracic, and/or lumbar spinal instrumentation, interbody vertebral cages, pedicle screws and the like. In alternative embodiments, products of manufacture of the invention comprise or are fabricated for in vivo applications including trauma, fixation devices including internal, external or rods. In alternative embodiments, products of manufacture of the invention comprise or are fabricated for in vivo applications as bone substitute material, bone void filler, and/or bone grafts.

In alternative embodiments, products of manufacture of the invention comprise or are fabricated for in vivo soft tissue applications, including e.g., catheters that need to be anchored in skin, implantable devices that promote cell growth, biosensors that reduce fibrotic capsule which blocks electrical/chemical signal.

Figure 8:
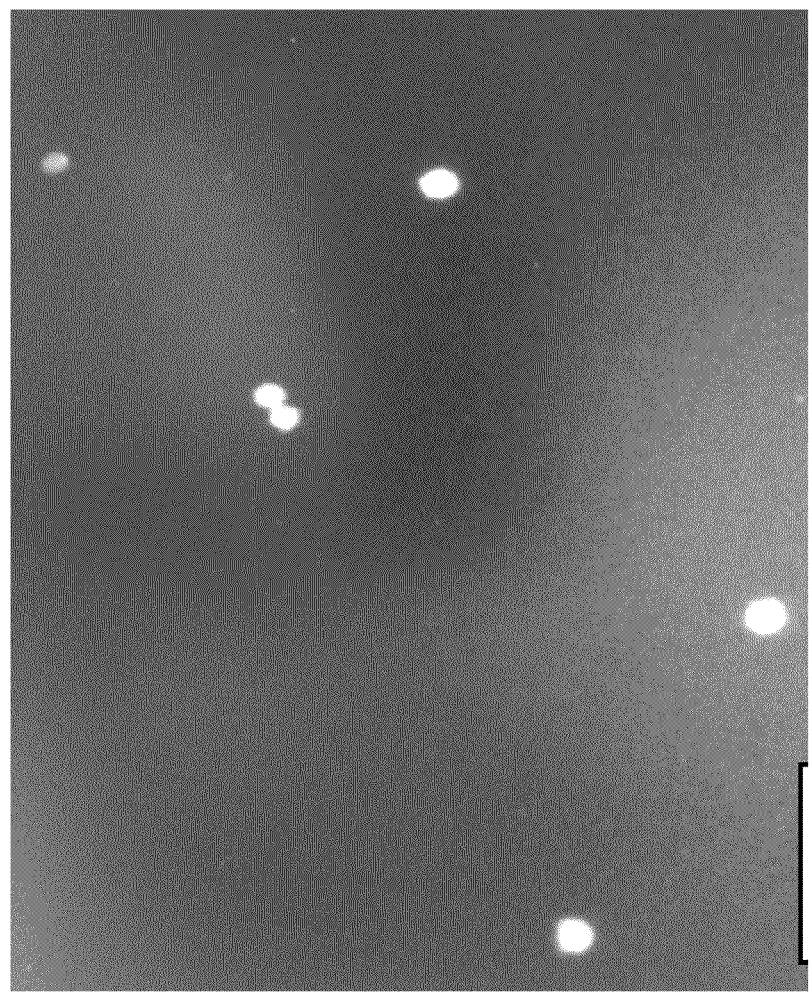
FIG. 8 illustrates a 48 hour culture with mouse osteoblast cells (MCT3-E1) on PEEK substrate with no patterning, as discussed in detail, below.

FIG. 8 illustrates that there was low osteoblast viability and poor cell spreading on as-received commercial PEEK substrate with no patterning and no Ti coating. FIG. 8 shows a 48 hour culture with mouse osteoblast cells (MCT3-E1) on PEEK substrate with no patterning. All the PEEK samples for this study was procured from Plastics International. The PEEK samples used for the experiments were 0.25 inch thick sheet form. No obvious cell adhesion and growth observed on PEEK surface, either flat or patterned.

Figure 9:
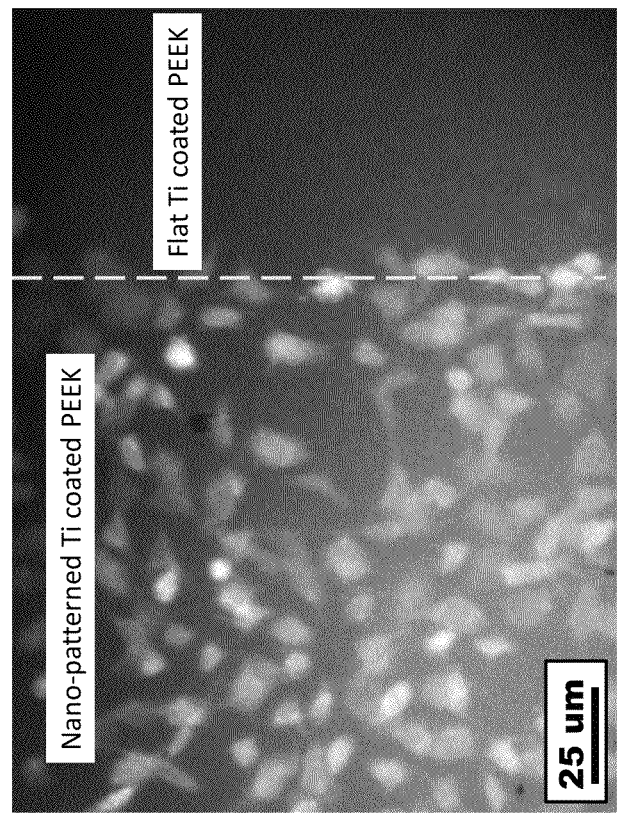
FIG. 9 illustrates osteoblast cell growth and spreading on 20 nm Ti Coated PEEK, as discussed in detail, below.

FIG. 9 illustrates osteoblast cell growth and spreading on 20 nm Ti Coated PEEK; PEEK was nanoimprinted at 400 nm diameter and 100 nm height+20 nm Ti sputter coated. Mouse osteoblast cell at 48 hrs culture period were used. No cell adhesion or growth on PEEK, no cell adhesion or growth on flat Ti coated PEEK, but lots of osteoblast cells are observed adhering/growing on 20 nm Ti coated, nano-patterned PEEK.

Figure 10:
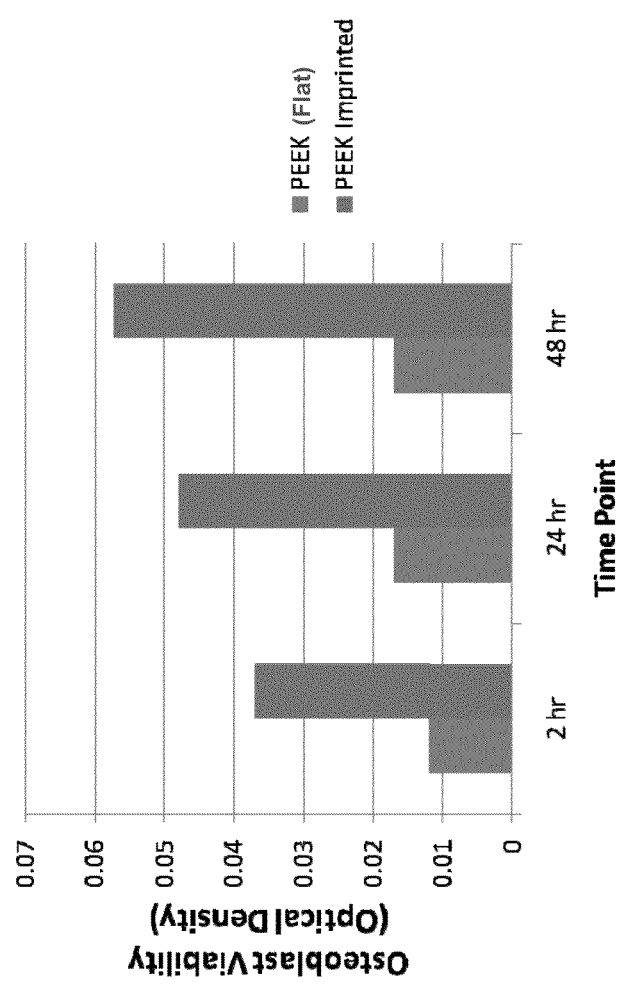
FIG. 10 graphically illustrates data showing the comparative osteoblast cell density over 48 hours (hrs), as discussed in detail, below.

FIG. 10 illustrates data showing the comparative osteoblast cell density over 48 hours (hrs); the MTT assay measured cell viability as optical density; unpatterned PEEK (flat) vs nano-imprinted pattern shown.

Figure 11:
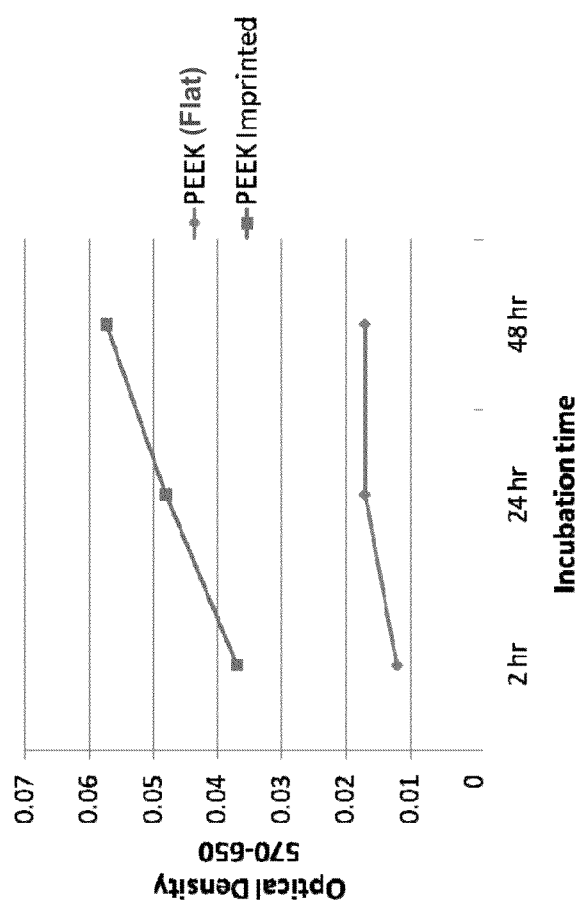
FIG. 11 graphically illustrates data showing the comparative osteoblast cell density after cell culture on flat unpatterned PEEK+Ti coated, versus (vs) nano-imprinted patterned PEEK+Ti coated shown at a 48 Hrs cell culture period, as discussed in detail, below.

FIG. 11 illustrates data showing the comparative osteoblast cell density after cell culture; Flat unpatterned PEEK+Ti coated, versus (vs) nano-imprinted patterned PEEK+Ti coated shown at a 48 Hrs cell culture period.

In alternative embodiments, a "patterned PEEK" design has clinical applications, e.g., in orthopedics. In alternative embodiments, patterned PEEK with a Ti coating yielded highly favorable osteoblast cell viability and cell spreading. 20 nm Ti thickness performed better than 5 nm Ti layer; cells preferred the patterned surfaces to the flat surface.

Figure 12:
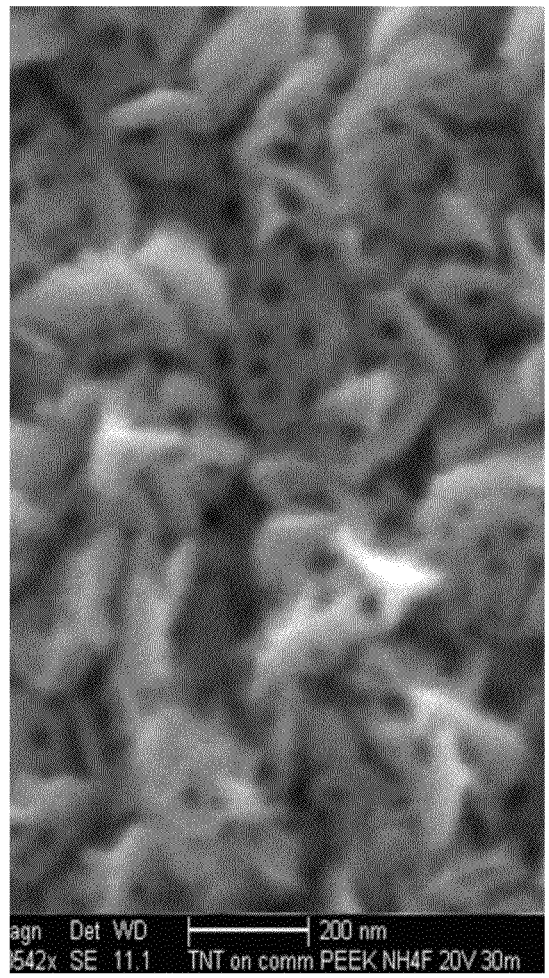
FIG. 12 illustrates an image of $TiO_2$ nanotubes/nanopores formed by anodization on sputter coated, 1 μm thick Ti film on flat commercial PEEK, as discussed in detail, below.

FIG. 12 illustrates an image of $TiO_2$ nanotubes/nanopores formed by anodization on sputter coated, 1 μm thick Ti film on flat commercial PEEK. Flat Ti film alone on PEEK did not provide much osteoblast cell adhesion and growth, TiO2 nanotube/nanopore formation induced strong cell adhesion.

Figure 13:
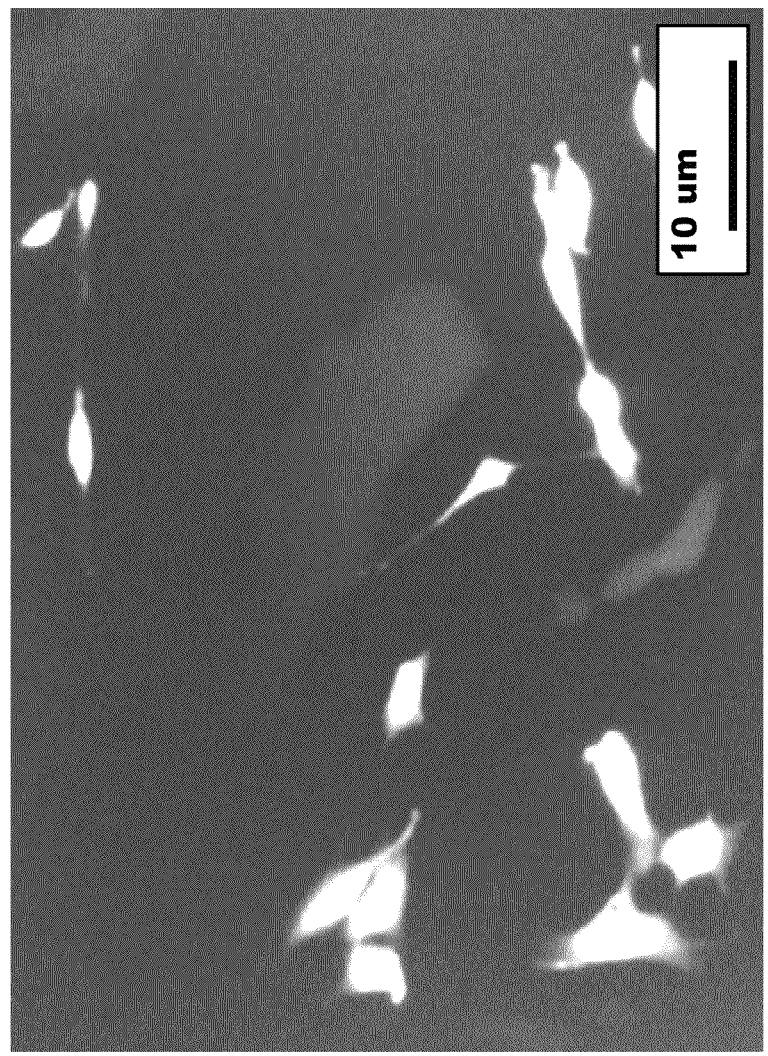
FIG. 13 illustrates osteoblast cell growth and spreading on TiO2 nanotube coated PEEK at 24 hrs culture, as discussed in detail, below.

FIG. 13 illustrates osteoblast cell growth and spreading on TiO2 nanotube coated PEEK at 24 hrs culture; the figure shows FDA staining under fluorescent microscopy at a 24 hour time point. For TiO2 nanotube formation from the Ti film added on the PEEK surface, the Ti coated PEEK (approximately 1 micrometer thick Ti sputter coated) was anodized in an ethylene glycol based solution (0.3 wt. % ammonium fluoride (NH4F) and 2 vol % water).

The anodization was done at 20 V for a 30 minute duration. The samples were then cut into 0.5 cm×0.5 cm squares and seeded with MCT3-E1 mouse osteoblast cells at passage 7. Each sample received 1 milliliter containing 50,000 cells in osteogenic media. Osteoblast cell viability was evaluated at 24 hr and 48 hr timepoints with an MTT assay and FDA staining for fluorescent microscopy.

In one embodiment, nano-patterned PEEK coated with titanium is radiolucent (partly transparent to medical X-ray). In general, X-rays from about 0.12 to 12 keV (10 to 0.10 nm wavelength) are classified as "soft" X-rays, and from about 12 to 120 keV (0.10 to 0.010 nm wavelength) as "hard" X-rays, due to their penetrating abilities. We utilized 18 keV X-ray, slightly penetrating x-ray suitable for medical uses.

Figure 14:
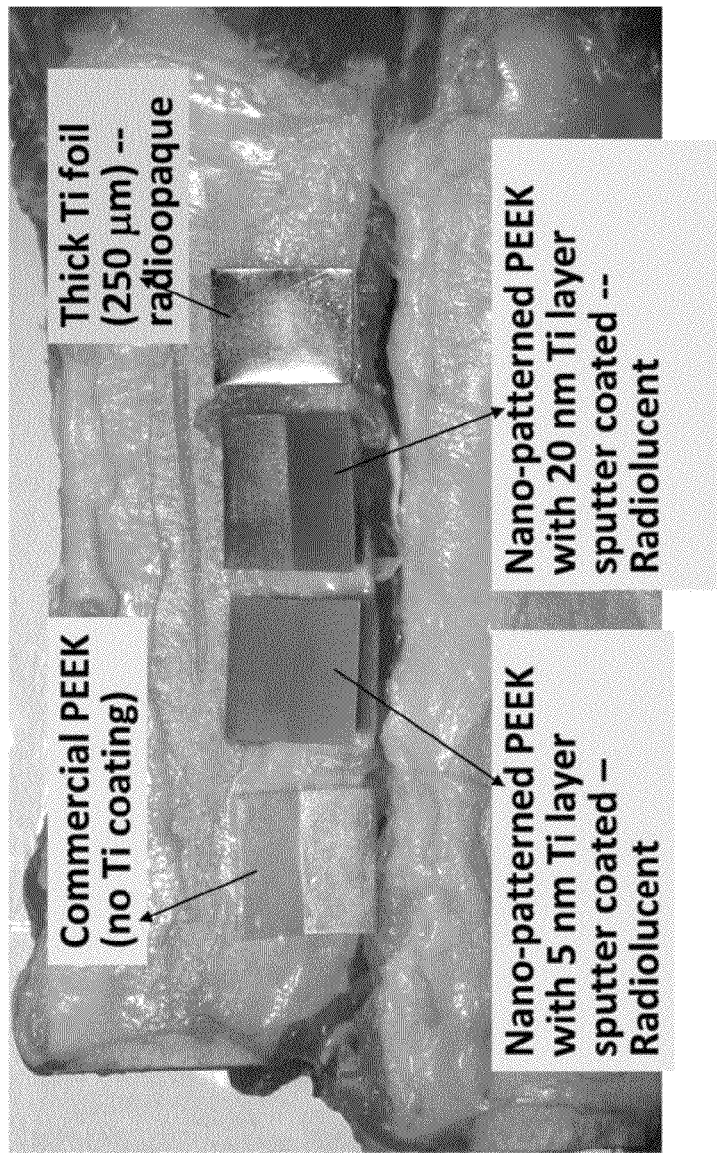
FIG. 14 illustrates an image of PEEK and Titanium (Ti) implant materials in Porcine Rib; sample size about 2.5×2.5 cm; note—the horizontal line in the middle of some samples is just the folding line in the PEEK, as discussed in detail, below.

FIG. 14 illustrates an image of PEEK and Titanium (Ti) implant materials in Porcine Rib; sample size about 2.5×2.5 cm; note—the horizontal line in the middle of some samples is just the folding line in the PEEK.

Figure 15:
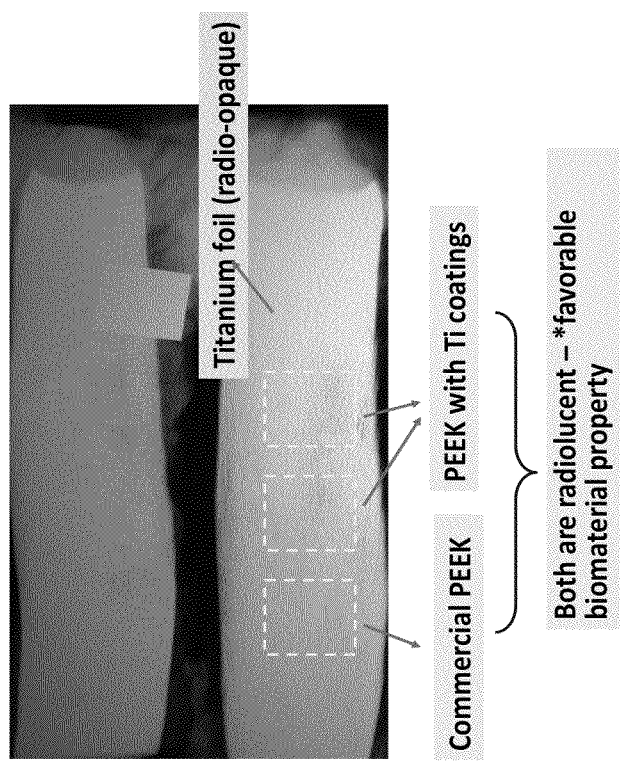
FIG. 15 illustrates an X-ray image showing that the Ti coated PEEK implants are radiolucent, as discussed in detail, below.

FIG. 15 illustrates an X-ray image showing that the Ti coated PEEK implants are radiolucent.

In alternative embodiments, nano-patterned PEEK with a 5 nm or 20 nm layer of titanium is radiolucent, and allows x-ray analysis of implant structures and its evolution in vivo or in patients having the inventive, improved PEEK implants. Radiolucency is an important biomaterial property for unobstructed visualization during implantation and post-surgical evaluation for best patient care practices.

Figure 16:
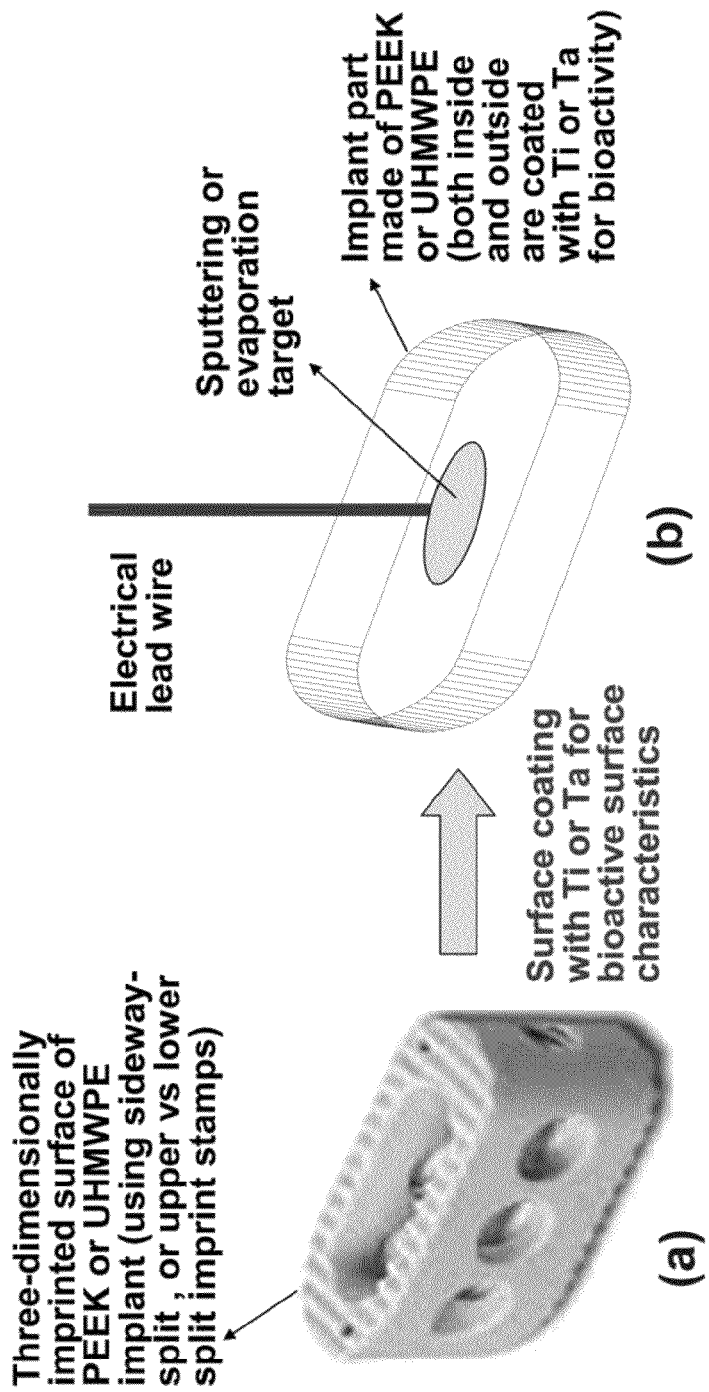
FIG. 16(a) illustrates three-dimensionally imprinted surface of a PEEK, PEKK, UHMWPE, thermoplastic polymer as set forth in Table 1, any combination thereof or equivalent material thereof, implant using sideway-split or upper versus lower split imprint stamps.
FIG. 16(b) illustrates both the inside and the outside of the complex shaped imparts made of PEEK, PEKK, UHMWPE, etc., coated with a Ti or a Ta or other refractory metal and/or their oxide(s) for bioactivity; and in one embodiment a probe-shaped sputter or evaporator target can be inserted into the cavity geometry.

In alternative embodiments, the invention provides interbody fusion cages comprising nano-patterned PEEK, e.g. as illustrated in FIG. 16, which illustrates an interbody fusion cage by Interbody Innovations, Midland, Tex.

In alternative embodiments, the invention provides nano-patterned PEEK that is radiolucent and has a similar modulus of elasticity to bone; these embodiments have a number of applications in orthopedics, trauma, and even for soft tissue applications.

In alternative embodiments, the invention provides nano-patterned PEEK for orthopedic joint replacements, this embodiment comprises a material which bonds to bone and has excellent stiffness properties. Potential applications for this exemplary nano-patterned PEEK include any medical devices which interface directly with bone including hip stems, knee implants, and shoulder replacements.

In alternative embodiments, the invention provides nano-patterned PEEK for craniofacial implants; these nano-patterned PEEK of the invention can be used for maxillofacial clinical applications where an osseoinductive material is desired. This includes oral implants, especially for applications in the lower jaw where bone density is poor.

In alternative embodiments, the invention provides nano-patterned PEEK for spinal applications, e.g., as an interbody support cage which can provide mechanical support between in the cervical, thoracic, and lumbar vertebrates.

In alternative embodiments, the invention provides nano-patterned PEEK for applications in the spine, e.g. including spinal fixation devices (i.e. pedical screws, rods, other support structures) where bonding is desired to bone for permanent anchorage.

In alternative embodiments, the invention provides nano-patterned PEEK for use in trauma, where rapid healing and bonding to bone is desired. This includes both internal and external fixation devices to fix broken bones. In alternative embodiments, the invention provides nano-patterned PEEK for areas of trauma that are quickly growing, e.g. for military applications where wounded soldiers can recover quicker from orthopedic injuries.

In alternative embodiments, the invention provides nano-patterned PEEK for soft tissue applications, e.g., where PEEK is beginning to be used for soft tissue repair in arthroscopy because the polymer has more favorable properties with soft tissue than metal. In alternative embodiments, with favorable cell growth properties, nano-patterned PEEK of the invention can enhance biocompatibility and overall tissue integration of devices.

In alternative embodiments, the invention provides nano-patterned PEEK include nano-patterned, thin metallized PEEK for use e.g. in catheters, devices which penetrate the skin, and coatings for biosensors for improved signal readings with less fibrotic encapsulation.

FIG. 16 illustrates: (a) Three-dimensionally imprinted surface of PEEK or UHMWPE implant (using sideway-split, or upper vs lower split imprint stamps), (b) Both inside and outside of the complex shaped implant parts made of PEEK or UHMWPE are coated with Ti or Ta (or other refractory metals and their oxides) for bioactivity, using a probe shaped sputter or evaporator target that can be inserted into the cavity geometry.

In alternative embodiments, these anodized or hydrothermally grown nanotubes grown on deposited Ti film on PEEK, UHMWPE or other polymer implant surface are micro or macro patterned so that 50% or less of the surface area of PEEK or UHMWPE is covered by TiO2 nanotubes for enhanced x-ray radiolucent properties.

Referring to FIG. 16: FIG. 16(a) illustrates a three-dimensionally imprinted surface of an PEEK or UHMWPE implant of the invention. In alternative embodiments, nanostructure formation on the surface of complicated structures such as the vertical wall of a cavity are made (accomplished) by using sideway or vertically split dies or nano-imprint stamps, e.g., with a pair of stamps one facing the outer wall and the other facing the interior wall in FIG. 16. Shown in FIG. 16(b) is an illustration of a method for coating such interior surface (coating of inside surface is more difficult than outer surface), e.g., using a probe shaped sputter or evaporator target device that can be inserted into the cavity geometry.

FIG. 17 illustrates: re-entrant Ti or TiO2 coating: (a) Peek or ultra high molecular weight poly ethylene (UHMWPE) implant with surface pores (e.g., made by warm imprinting, sand blasting, masked etching, etc.), (b) Optional warm compressive plastic deformation to partially squash the polymer implant surface and induce re-entrant pore geometry on peek or UHMWPE, (c) Ti coating (or Ta, Zr, Hf coating) or their oxide version on re-entrant shape pore surface for enhanced mechanical locking.

In alternative embodiments, it is important to ensure good adhesion of Ti and other coating layer to the PEEK and related polymer implant surfaces. One embodiment to enhance such mechanical stability against layer peeling is to introduce a re-entrant pore geometry, as illustrated in FIG. 17. As the coating material such as Ti is continuous, the re-entrant pore will have some effect of mechanical constraint or locking of the film to minimize the initiation of peeling off. The re-entrant pores can have an entrance diameter (an average diameter if it is not circular) which is smaller than the maximum average diameter within the pore. In alternative embodiments, a ratio of the maximum inner-pore diameter to the entrance diameter is at least 1.05, or at least 1.20.

Referring to FIG. 17, the diagram schematically illustrates an exemplary method of forming re-entrant pores, followed by Ti or TiO2 coating. In FIG. 17(a), a peek or ultra high molecular weight poly ethylene (UHMWPE) implant with surface pores (e.g., made by warm imprinting, sand blasting, masked etching, etc.), which is then optionally warm compressed in the vertical direction to induce plastic deformation to partially squash the polymer implant surface and induce re-entrant pore geometry on peek or UHMWPE as illustrated in FIG. 17(b). After the formation of re-entrant pores, Ti coating (or Ta, Zr, Hf coating) or a coating of their oxide version on re-entrant shape pore surface is conducted as described in FIG. 17(c) for enhanced mechanical locking.

It should be understood that the invention can be practiced with modification and alteration within the spirit and scope of the appended claims. The description is not intended to be exhaustive or to limit the invention to the precise form disclosed. It should be understood that the invention can be practiced with modification and alteration and that the invention be limited only by the claims and the equivalents thereof.

What is claimed:

1. A product of manufacture comprising an internal cavity having an inner wall and an outer wall, the product of manufacture further comprising:

(a) a thermoplastic polymer comprising a plurality of nano-imprints, wherein at least a portion of the plurality of nano-imprints are formed using a pair of nano-imprint stamps, wherein the first of the pair of nano-imprint stamps faces the inner wall and the second of the pair of nano-imprint stamps faces the outer wall, wherein at least a portion of the plurality of nano-imprints each have a re-entrant pore geometry that is formed using a process comprising a warm compression of the thermoplastic polymer; and (b) a biocompatible surface layer deposited on at least a portion of the thermoplastic polymer, wherein the biocompatible surface layer comprises any of a metal, a metal alloy, a stainless steel, and a ceramic, wherein the biocompatible surface layer includes a plurality of nanotubular structures that each have a diameter of approximately 5 to 1000 nanometers (nm).

2. The product of manufacture of claim 1, wherein at least approximately 50% of the biocompatible surface layer is covered by the plurality of nanotubular structures.

3. The product of manufacture of claim 1, wherein any of the biocompatible surface layer and the plurality of nanotubular structures comprise a material selected from the group consisting of:
(i) a material selected from the group consisting of a Ti, a Zr, a Hf, a Nb, a Ta, a Mo and a W metal;
(ii) a material selected from the group consisting of an oxide of a Ti, a Zr, a Hf, a Nb, a Ta, a Mo and W metal;
(iii) a material selected from the group consisting of an alloy of a Ti, a Zr, a Hf, a Nb, a Ta, a Mo and a W metal;
(iv) a material selected from the group consisting of a Si, a Si oxide, an Al, an Al oxide, a carbon, a diamond, a noble metal, an Au, an Ag, a Pt, an Ag oxide, and a Pt alloy,
(v) a plastic material,
(vi) a composite metal,
(vii) a ceramic,
(vii) a polymer, and
(viii) a combination thereof.

4. The product of manufacture of claim 1:
further comprising any of at least one of a bone cell, a liver cell, a kidney cell, a blood vessel cell, a skin cell, a periodontal cell, a periodontal tissue cell, a stem cell, an organ cell,
a fully differentiated osteoblast cell, a partially differentiated osteoblast cell, a mesenchymal stem cell (MSC), a human mesenchymal stem cell (hMSC), an embryonic stem cell, an adult stem cell, endothelial cells, adipocytes, fibroblastic cells, Kupffer cells, odontoblasts, dentinoblasts, cementoblasts, enameloblasts, odontogenic ectomesenchymal tissue, osteoblasts, osteoclasts, fibroblasts, a cell involved in odontogenesis or bone formation, a human cell, an animal cell, and a combination thereof.

5. The product of manufacture of claim 1, wherein the biocompatible surface layer includes any of a hydroxyapatite, a bio-degradable polymer, a bio-compatible cement, a bio-inert bone cement, a biological agent; a therapeutic composition, an osteogenic inducing agent, a growth factor, a collagen, a nucleic acid, an antibiotic, a hormone, a drug, a magnetic particle, a metallic particle, a ceramic particle, a polymer particle, a drug delivery particle and a combination thereof.

6. The product of manufacture of claim 1, wherein the plurality of nanotubular structures:
(a) are in the form of any of nanowires, nano-lines, nano-grooves, nanotubes, nanopores and a combination thereof; or
(b) are made by any of anodization, patterned chemical etching, and a combination thereof.

7. The product of manufacture of claim 1, wherein the plurality of nanotubular structures and spacing between adjacent nanotubular structures act as a nanodepot that stores any of a metal, an oxide, a hydroxyapatite, a bio-degradable polymer, a bio-compatible, a bio-inert bone cement, a cell, a stem cell, an osteogenic inducing agent, a biological agent, a therapeutic composition, a growth factor, a collagen, a nucleic acid, an antibiotic, a hormone, a drug, a magnetic particle, a metallic particle, a ceramic particle, a polymer particle, a drug delivery particle and a combination thereof.

8. A device comprising a product of manufacture of claim 1.

9. An implant comprising a product of manufacture of claim 1.

10. A product of manufacture of claim 1, fabricated for any of in vivo hard tissue applications, in vivo soft tissue applications, and in vivo hard tissue and soft tissue applications.

11. A product of manufacture of claim 1, fabricated for in vitro applications.

12. The product of manufacture of claim 1, wherein the thermoplastic polymer is any of PolyEther EtherKetone (PEEK), a PolyEtherKetoneKetone (PEKK), a PolyEther EtherKetone (PEEK), an ultra-high-molecular-weight polyethylene (UHMWPE), a combination thereof, and an equivalent material thereof.

13. The product of manufacture of claim 1, wherein:
the plurality of nanotubular structures comprise any of a metal, a metal alloy, a stainless steel, and a ceramic 14. The product of manufacture of claim 1, wherein the metal and the metal alloy comprises any of a Ti metal, a Zr metal, a Hf metal, a Nb metal, a Ta metal, a Mo metal, a W metal, a Ti alloy, a Zr alloy, a Hf alloy, a Nb alloy, a Ta alloy, a Mo alloy, a W alloy, a Ti oxide, a Zr oxide, a Hf oxide, a Nb oxide, a Ta oxide, a Mo oxide, W oxide, and a nitride.

15. The product of manufacture of claim 1, wherein the plurality of nanotubular structures are any of straight, curved, and bent.

16. The product of manufacture of claim 1, wherein the plurality of nanotubular structures are arranged as any of an array and a three-dimensional network scaffold.

17. The product of manufacture of claim 1,
wherein:
the thermoplastic polymer comprises a nano patterned PolyEther EtherKetone (PEEK) and the biocompatible surface layer comprises a layer of titanium (Ti) sputtered on a surface of the thermoplastic polymer.

18. The product of manufacture of claim 10, wherein the in vivo hard tissue applications include any of:
an orthopedic implant,
an orthopedic replacement,
a joint implant,
a joint replacement,
a hip stem,
a knee implant,
a shoulder replacement,
a dental implant,
a craniofacial implant;
a spine application,
a cervical instrumentation,
a thoracic instrumentation,
a lumbar spinal instrumentation,
an interbody vertebral cage,
a pedicle screw,
a bone substitute material,
a bone void filler,
a bone graft material, and
a combination thereof.

19. The product of manufacture of claim 10, wherein the in vivo hard tissue and soft tissue applications include any of:
a trauma application,
a fixation device,
an internal fixation device, an external fixation device, and
a rod.

20. The product of manufacture of claim 10, wherein the in vivo soft tissue applications include any of:
use with a catheter,
use with an implantable device that promotes cell growth, and
use with a biosensor that reduces a fibrotic capsule which blocks any of an electrical and a chemical signal.

21. The product of manufacture of claim 1, wherein the plurality of nanotubular structures each have a diameter of approximately 60 to 150 nm.

22. The product of manufacture of claim 1, wherein there is a spacing between the plurality of nanotubular structures of approximately 70 to 200 nanometers (nm).

23. The product of manufacture of claim 22, wherein there the spacing between the plurality of nanotubular structures is approximately 60 to 150 nanometers (nm).

24. The product of manufacture of claim 22, wherein there the spacing between the plurality of nanotubular structures is approximately 80 to 120 nanometers (nm).

25. The product of manufacture of claim 1, wherein the plurality of nanotubular structures are approximately 100 nanometers (nm) in diameter.

26. The product of manufacture of claim 1, wherein the plurality of nanotubular structures are approximately 80 to 120 nanometers (nm) in diameter.

27. The product of manufacture of claim 1, wherein the plurality of nanotubular structures each have a diameter of approximately 5 to 15 nm and approximately a 0.1 to 3 micrometer height.

28. The device of claim 8, wherein the device is a delivery device.

29. The product of manufacture of claim 1, wherein the product of manufacture is a composition.

30. The implant of claim 9, wherein the implant is any of a medical implant, an orthopedic implant, a joint implant, a joint replacement, a dental implant, a tooth implant, a knee implant, a hip implant, a shoulder implant, a joint implant, a joint replacement, a dental replacement, a tooth replacement, a knee replacement, a hip replacement, and a shoulder replacement.

31. The product of manufacture of claim 1, wherein the plurality of nanotubular structures each has a diameter of between approximately 80 to 100 nanometers (nm).

32. The product of manufacture of claim 1, wherein the plurality of nanotubular structures each has a diameter of approximately 8 nanometers (nm).

33. The product of manufacture of claim 1, wherein the product of manufacture comprises an internal cavity comprising vertical walls made by using sideway or vertically split dies or a pair of nano-imprint stamps, one facing the outer wall and the other facing the interior wall.

34. The product of manufacture of claim 2, wherein substantially all of the biocompatible surface layer is covered by the plurality of nanotubular structures.

35. The product of manufacture of claim 1, wherein the re-entrant pore geometry comprises an entrance diameter, or an average diameter if the nano-imprint is not circular, which is smaller than the maximum average diameter within the nano-imprint.

36. The product of manufacture of claim 1, wherein the process comprising the warm compressive comprises applying a warm compressive plastic deforming force in a vertical direction to partially squash at least a portion of the thermoplastic polymer to the re-entrant pore geometry.

37. The product of manufacture of claim 35, wherein the re-entrant pore geometry comprises a nano-pore, wherein a ratio of a maximum inner-pore diameter to the entrance diameter is at least 1.05.

38. A product of manufacture, comprising:
(a) a thermoplastic polymer comprising a nano-imprinted surface, wherein at least a portion of the nano-imprinted surface comprises a plurality of nano-imprints; and
(b) a biocompatible surface layer deposited on at least a portion of the thermoplastic polymer, wherein the biocompatible surface layer comprises any of a metal, a metal alloy, a stainless steel, and a ceramic, wherein the biocompatible surface layers includes a plurality of nanotubular structures that each have a diameter of approximately 8 nanometers (nm), further wherein the product of manufacture comprises an internal cavity comprising vertical walls made by using a pair of nano-imprint stamps, one facing an outer wall and the other facing an inner wall.

* * * * *